(12) United States Patent
Prystupa

(10) Patent No.: US 11,353,439 B2
(45) Date of Patent: Jun. 7, 2022

(54) METHOD FOR BONE SCAN IN MEAT

(71) Applicant: 7386819 Manitoba Ltd., Winnipeg (CA)

(72) Inventor: David Prystupa, Pinawa (CA)

(73) Assignee: 7386819 Manitoba Ltd., Winnipeg (CA)

( * ) Notice: Subject to any disclaimer, the term of this patent is extended or adjusted under 35 U.S.C. 154(b) by 190 days.

(21) Appl. No.: 16/782,234

(22) Filed: Feb. 5, 2020

(65) Prior Publication Data
US 2020/0217831 A1 Jul. 9, 2020

Related U.S. Application Data

(63) Continuation of application No. 15/327,715, filed as application No. PCT/CA2015/050678 on Jul. 21, 2015, now abandoned.
(Continued)

(51) Int. Cl.
*G01N 33/12* (2006.01)
*G01N 21/3563* (2014.01)
(Continued)

(52) U.S. Cl.
CPC ......... *G01N 33/12* (2013.01); *A22C 17/0073* (2013.01); *G01N 21/3563* (2013.01);
(Continued)

(58) Field of Classification Search
CPC .... G01N 33/12; G01N 21/3563; G01N 21/65; G01N 21/94; G01N 29/07;
(Continued)

(56) References Cited

U.S. PATENT DOCUMENTS 3,877,818 A * 4/1975 Button ...................... G01J 3/12
356/416
5,641,907 A * 6/1997 Haagensen ............ A22B 5/007
73/620
(Continued)

FOREIGN PATENT DOCUMENTS

CN 102564964 A 7/2012

OTHER PUBLICATIONS

Meat Quality Evaluation by Hyperspectral Imaging Technique: An Overview, Dec. 31, 2012; Gamal Elmasry et al., Critical Reviews in Food Sceince and Nutrition.
(Continued)

*Primary Examiner* — Peter J Macchiarolo
*Assistant Examiner* — John M Royston
(74) *Attorney, Agent, or Firm* — Adrian D. Battison; Ade & Company Inc.; Michael R. Williams

(57) ABSTRACT

A method and device for detection of bone in meat identifies fragments larger than about 1 mm using spectral optical imaging and ultrasound. Spectral imaging can detect foreign material proximate to the surface and ultrasound can detect material within the sample. The sample is irradiated by light and reflected light or Raman scattered light measured. The sample is similarly irradiated by ultrasound and reflected or transmitted sound waves give a set of amplitude data points, which include temporal delay. These data points are then processed by statistical methods to derive a set of vectors in n-dimensional space, which are compared to a calibrated data set of derived vectors which have distinct identifying loci for each type of surface, are indicative of the presence or absence of defects.

17 Claims, 10 Drawing Sheets

Related U.S. Application Data

(60) Provisional application No. 61/999,206, filed on Jul. 21, 2014.

(51) Int. Cl.
*G01N 21/65* (2006.01)
*A22C 17/00* (2006.01)
*G01N 21/94* (2006.01)
*G01N 29/07* (2006.01)
*G01N 21/35* (2014.01)
*G01S 15/88* (2006.01)
*G01S 7/52* (2006.01)

(52) U.S. Cl.
CPC .............. *G01N 21/65* (2013.01); *G01N 21/94* (2013.01); *G01N 29/07* (2013.01); *G01N 2021/3595* (2013.01); *G01N 2201/129* (2013.01); *G01S 7/52036* (2013.01); *G01S 15/88* (2013.01)

(58) Field of Classification Search
CPC ...... G01N 2021/3595; G01N 2201/129; A22C 17/0073; G01S 7/52036; G01S 15/88
See application file for complete search history.

(56) References Cited

U.S. PATENT DOCUMENTS

| | | | |
|---|---|---|---|
| 6,324,901 B1* | 12/2001 | Fluh | G01N 29/032 73/598 |
| 2003/0098409 A1* | 5/2003 | Bond | G01N 21/59 250/223 R |
| 2003/0098796 A1* | 5/2003 | Bond | G01N 29/11 340/627 |
| 2005/0068535 A1* | 3/2005 | Bond | A22C 21/00 356/433 |

OTHER PUBLICATIONS

Overconstrained Library-Based Fitting Method Reveals Age-and Disease-Related Differences in Transcutaneous Raman Spectra of Murine Bones; Jul. 31, 2013; Jason R. Maher et al., Journal of Biomedical Optics.

Application of Raman Spectroscopy in Bone Research; Sep. 30, 2010; Shen Jing et al.

* cited by examiner

METHOD FOR BONE SCAN IN MEAT

This application is a continuation of application Ser. No. 15/327,715 which is a 371 of PCT/CA2015/050678 filed Jul. 21, 2015 and claims benefit under 35 USC 119(e) from Provisional application 61/999,206 filed Jul. 21, 2014.

The present invention pertains to the detection of small objects wholly or partly embedded in soft tissue. Generally, although not essentially, the objects are bone fragments or very small bones in meat. Large bones are not a problem because they are easily visible. Commercially, most typically, the meat is chicken breast, as the bone tends to fragment when the breast is deboned. The invention can also be applied to poultry, fish, and other meats liable to contain bone fragments or very small bones.

BACKGROUND OF THE INVENTION

Bone fragments or hard objects larger than 1 mm in size, which may be present in food products, pose a risk to human health. Consequently bone fragments pose both a regulatory risk and a litigation risk to food processing operations. For a bone detection method to be commercially viable, the method must be able to reliably detect bone fragments at the small end of the range. Surface defects are more common, embedded defects less so.

Bone is a composite matrix with a variety of morphologies. The major structural components of bone are hydroxyapatite $Ca_5(PO_4)_3OH$ and type I collagen. Collagen is also the primary constituent of cartilage, which is often closely associated with bone. Significant amounts of lipid and hydration water are also associated with bone in the native state. Other biomolecules are present, but not in sufficient quantity to have a significant effect on the types of measurements discussed herein. The technical problem is to find bone in a meat matrix composed of protein and lipid.

The earliest approaches to the problem involved variants of the candling (backlighting) method to processing fish fillets. In this approach, the meat sample is backlit and variations in the transmitted intensity indicate the presence of an absorbing object (usually bone) in the meat. The primary weakness of this method is that tissue scatters photons at every refractive index discontinuity, effectively on the scale of cellular dimensions. Because of scattering at cell surfaces, information about the direction of propagation of a photon is almost completely randomized within approximately 3 mm of travel. Photon diffusion models best describe the propagation of photons through tissue. To complicate matters further, an increase in the thickness of flesh has the same attenuating effect as the presence of a bone beneath the surface. The candling method is thus limited to thin samples with uniform thickness. While it is possible in laboratory conditions to measure photons that travel from a pulsed laser without scatter through up to 10 cm of tissue by time gating methods, the directly transmitted fraction is on the order of $10^{-12}$ of the incident intensity. The cost and sophistication required to extend the range of the candling method render it unfit for the food processing applications contemplated by the present invention.

U.S. Pat. No. 7,363,317 discloses a candling method using 500 nm to 600 nm backlighting with a planar array of LEDs and off axis ultrasound scattering added to provide some sensitivity to defects in the bulk. The light detector (camera) is aligned with the incident light. The method described measures attenuation between an acoustic transmitter and a receiver oriented to capture off axis scattering. The Mei theory of scattering applies in the regime where the size of a scattering object is close to the wavelength of the scattered wave. In this regime scattering can be highly directional, and detection depends on the fortuitous presence of a detector at the proper scattering angle. Secondly, the signal from a small defect can be lost within a larger signal from texture within the meat matrix.

U.S. Pat. No. 4,631,413 discloses an elegant method wherein fluorescence from bone, cartilage and fat is excited by UV radiation. This method has the advantage that the fluorescence from the protein matrix is minimal. High amplitude indicates bone cartilage or fat, while low amplitude indicates flesh.

U.S. Pat. No. 7,460,227 describes a later variant of the UV fluorescence method, which measures fluorescence at two wavelengths to improve discrimination between cartilage and bone. The UV fluorescence method, like the candling method is limited to thin samples due to the high photon scattering cross section of flesh. In an industrial setting, there is a need to protect workers from UV radiation used in this method.

Most prior attention to the problem of detecting bone fragment has focused on the development of x-ray modalities, which have much smaller scattering cross sections than photons at longer wavelengths and can thus directly image defects deeply buried in tissue. Further, x-ray scattering depends on the electron density and is thus more sensitive to heavy elements such as Ca in bone than to light elements H, C, O and N in the bulk matrix. The x-ray method has limited capability to detect weakly mineralized bones and cartilage or account for variation in sample thickness. Historically, this has driven x-ray systems from simple direct imaging toward sophisticated computed tomography systems. The x-rays measure electron density, which is higher in heavier atoms, especially Ca and P, which are both constituents of bone. A number of US patents describe this approach as set out as follows.

U.S. Pat. No. 5,585,603 mass of object
U.S. Pat. No. 6,023,497 tuned detector
U.S. Pat. No. 6,299,524
U.S. Pat. No. 6,512,812 single emitter
U.S. Pat. No. 6,546,071 single emitter
U.S. Pat. No. 6,563,904 single emitter
U.S. Pat. No. 6,600,805 2 sources
U.S. Pat. No. 6,370,223 2 sources plus laser profile to factor thickness out
U.S. Pat. No. 6,449,334 2 sources, 2 energies
U.S. Pat. No. 6,597,759 2 sources, 2 energies
U.S. Pat. No. 6,597,761 CT
U.S. Pat. No. 5,182,764 CT
U.S. Pat. No. 6,430,255 CT
U.S. Pat. No. 6,590,956 CT
U.S. Pat. No. 6,018,562 CT
U.S. Pat. No. 7,060,981 CT increased speed by using multiple sources at increased cost CT, computed tomography measures wave intensity at multiple angles and back calculates an image. Several problems remain, even with the most recent CT systems. There is a requirement to shield workers from x-rays and to document radiation exposure daily. X-ray emitters use high voltage and are operated in a damp environment posing further risk to workers. The high capital cost and high cost of maintenance have limited the adoption of x-ray methods in food processing applications.

SUMMARY OF THE INVENTION

According to a first aspect of the invention there is provided a method for detecting defects in a meat sample on a production line, comprising the steps of:

emitting at least one wavelength of light onto an area of said meat sample;

receiving light reflected from said area of said meat sample measuring the amplitude of said reflected light;

emitting at least one frequency of ultrasound onto said area of said meat sample and receiving ultrasound signals returned from said meat sample;

and in a data processor comparing the amplitudes of said reflected light for each said area of said meat sample by multivariate analysis of amplitudes of a plurality of distinct wavelengths and determining from said multivariate analysis the presence of surface defects in said meat sample using a statistical model;

wherein the statistical model calculates a cumulative probability that a defect exists within said area based on measurements of wavelength dependence, an edge probability obtained from a gradient of said amplitudes, and said acoustic signals loaded into a common data vector.

None of the prior art discusses the use of acoustic measurement systems so that the new claim is novel over the prior art.

The new claim is NOT MERELY a combination of optical measurements and acoustic measurements; but combines these in a unique manner where:

-a- the signals are used in combination with an edge probability calculated from a gradient or derivative of the amplitudes of the optical signals;

-b- the values are loaded into a common data vector so as to use statistical analysis on the data commonly.

The present inventor has found that this analysis system using this data in this manner allows the detection of defects in a manner which separate analysis using one or both of optical and acoustic measurements cannot.

The methods as described in more detail hereinafter may provide one or more of the following features, objects or advantages:

The principal object is to provide a robust and economical means to detect small defects both on the surface and deep within the bulk of meat.

One principal object is to provide a spectral imaging system and method to detect surface defects on a meat sample, replacing meat inspectors on a production line.

One principal object is to provide an acoustic ultrasound system and method to detect bones on and in on a meat sample.

Another principal object is to provide a device for detecting defects in a meat sample on a production line, having at least one light emitter and at least one optical detector to register optical signals which supplies the signals as data to a data processor, which processes the data so as to indicate the presence of defects in said meat samples, the data processor has an associated indicator which indicates the presence of a defect in said meat sample.

Another principal object is to provide a device, which has at least one ultrasound emitter and at least one acoustic detector to register acoustic signals, both the optical and acoustic detectors supply signals as data to a data processor.

A subsidiary object is to provide a device wherein the light emitter is selected from the group consisting of a broadband white light source, a light source with at least two types of LEDs of different wavelengths, a quasi-monochromatic laser light source to excite Raman scattered radiation, a quasi-monochromatic LED light source filtered through at least one bandpass filter to excite Raman scattered radiation, a light source with at least two strobed LEDs of different wavelengths, a near infrared light source and an ultraviolet light source to excite Raman scattered radiation.

A further subsidiary object is to provide a device with a light source with at least two types of LEDs of wavelengths between 620 and 640 and 720 and 760 nm.

A further subsidiary object is to provide a device with a light source with at least three types of LEDs of wavelengths between 540 and 570, 620 and 640 and 720 and 760 nm.

A further subsidiary object is to provide a device with an ultraviolet light source that emits light of wavelength between 200 and 220 nm to excite Raman scattering.

A further subsidiary object is to provide a device wherein a quasi-monochromatic laser light source emits light of wavelength visible light and infrared light at selected from the group consisting of 488, 515, 532, 594, 633, 635, 650, 660, 670, 785, 808, 830, 850, 980, and 1064 nm to excite Raman scattering.

A further subsidiary object is to provide a device wherein a quasi-monochromatic LED light source emits light of wavelength visible light and infrared light at selected from the group consisting of 488, 515, 532, 594, 633, 635, 650, 660, 670 785, 808, 830, 850, 980, and 1064 nm to excite Raman scattering filtered through at least one bandpass filter to excite Raman scattering.

A further subsidiary object provides a device wherein a near infrared light source emits light of wavelength between 900 and 2600 nm.

A further subsidiary object provides an ultrasound emitter, which is a transverse array of transducers.

A further subsidiary object is to provide an array of ultrasound transducers each separately controlled by a logic processor actuating a switching circuit power for a power converter for each said transducer.

A further subsidiary object is to provide an optical detector is selected from the group consisting of a transverse line scan detector comprising pixels, a focal plane array of pixels, and said pixels measuring light amplitudes.

A further subsidiary object is to provide when the optical detector is a focal plane array of pixels, an associated wave length selector.

A further subsidiary object is to provide an associated wavelength selector selected from the group consisting of a prism, a diffraction grating, and a bandpass filter, where the focal plane array comprises a plurality of separate transverse arrays of pixels, each separate array corresponding to a different selected wavelength.

A further subsidiary object is to provide an associated wavelength selector which is a Fourier transform spectrometer with an optical detector selected from the group consisting of an optical detector integral to said Fourier transform spectrometer, and an optical detector connected to said Fourier transform spectrometer through an auxiliary detector connection.

A further subsidiary object is to provide an acoustic detector is selected from the group consisting of the ultrasound emitter comprising a transverse array of transducers, and a separate array of acoustic transducers acoustically insulated from said ultrasound emitter, where the acoustic detector measuring acoustic amplitudes and time of flight of each acoustic amplitude.

A further subsidiary object is to provide a data processor to receive a plurality of light amplitudes corresponding to a sample area of said meat sample, and the data processor using multivariate analysis generates orthogonal n-dimensional data vectors, by projection onto n eigenvectors from a calibration set, and compares these data vectors with vectors in a calibration set, to determine whether they correspond to bone, cartilage, fat, flesh or skin, or contaminant for each sample area of the sample, when bone is identified, a logic signal is sent to actuate a pass-fail gate stopping the sample, otherwise no logic signal is sent.

A further subsidiary object is to provide that the data processor additionally identifies the amplitudes of neighboring areas to said sample area, abutting directly and diagonally, for each wavelength, the amplitudes of the area and neighboring areas for all the wavelengths are subjected to multivariate analysis, which generates orthogonal n-dimensional data vectors, by projection onto n eigenvectors from a calibration set, and compares these data vectors with vectors in a calibration set, which additionally determine the presence of edges between sample areas, when an edge is identified, a logic signal is sent to actuate a pass-fail gate stopping the sample, otherwise no logic signal is sent.

A further subsidiary object is to provide that the data processor receives a plurality of acoustic amplitudes and times of flight of said amplitudes corresponding to a sample area of said meat sample, said data processor compares said amplitudes to standard amplitudes to determine the presence of bone in said sample, when bone is present, a logic signal is sent to actuate a pass-fail gate stopping the sample, otherwise no logic signal is sent.

A further subsidiary object is to provide a data processor which mean centers and normalizes said amplitudes to standard deviation for each wavelength.

Another principal object is to provide a method for detecting defects in a meat sample on a production line, comprising the steps of emitting at least one wavelength of light onto an area of said meat sample, receiving light reflected from said area of said meat sample, measuring the amplitude of said reflected light, comparing the amplitudes of said reflected light for each area of said meat sample by multivariate analysis, determining from said multivariate analysis the presence of surface defects in said meat sample.

A subsidiary object is to provide a method comprising the additional steps of, emitting at least one frequency of ultrasound onto an area of said meat sample, receiving ultrasound returned from said meat sample, measuring the amplitudes and times of flight of said returned ultrasound, comparing the amplitudes and times of flight of said returned ultrasound for each area of said meat sample by multivariate analysis, determining from said multivariate analysis the presence of surface and internal defects in said meat sample.

A further subsidiary object is to provide a method comprising the additional steps of comparing the amplitudes of said reflected light for each area of said meat sample and the amplitudes and times of flight of said returned ultrasound for each area of said meat sample by multivariate analysis, determining from said multivariate analysis the presence of surface and internal defects in said meat sample.

A further subsidiary object is to provide a method of, wherein a single wavelength of light is emitted and the reflected light is Raman scattered comprising the additional step of dispersing said Raman scattered light through a wavelength selector to separate the Raman scattered light into distinct wavelengths, and the further additional step of measuring the amplitudes of said distinct wavelengths.

A further subsidiary object is to provide a method wherein said single wavelength to excite Raman scattered light is quasi-monochromatic and selected from ultraviolet in the wavelength range of 200 to 220 nm and visible light and infrared light at 488, 515, 532, 594, 633, 635, 650, 690, 670, 785, 808, 830, 850, 980, and 1064 nm.

A further subsidiary object is to provide a method wherein said at least one wavelength of light is broad band white light, and comprising the additional step of dispersing said reflected light through a wavelength selector to separate the reflected light into distinct wavelengths and the further additional step of measuring the amplitudes of said distinct wavelengths. A further subsidiary object of the invention is to provide a method wherein said at least one wavelength of light is near infrared wavelength selected from the range of 900 to 2600 nm. A further subsidiary object of the invention is to provide a method of wherein said at least one wavelength of light comprises at least two separate wavelengths.

A further subsidiary object is to provide a method comprising the steps of emitting at least two separate wavelengths at separate times, and the steps of measuring said amplitudes of reflected light at separate times.

A further subsidiary object is to provide a method, wherein at least two separate wavelengths comprise between 620 and 640 and 720 and 760 nm. A further subsidiary object of the invention of the invention is to provide a method wherein at least two separate wavelengths comprise between 540 and 570, 620 and 640 and 720 and 760 nm. These wavelengths may be and conveniently are non-coherent light emitted by non-coherent LEDs, typically of wavelength bands 540 to 570, 620 to 640, 720 to 760 nm. The wavelengths may be and conveniently are non-coherent light emitted by non-coherent LEDs, typically of wavelength bands 540 to 570, 620 to 640, 720 to 760 nm. In the 540 to 570 nm band the central value can be anywhere from 540 to 570 nm; in the 620 to 640 nm band the 630 nm central value is optimal, in the 720 to 760 nm band the central value can be anywhere from 720 to 760 nm.

A further object is to provide a device for detecting defects in a meat sample on a production line, which comprises at least one ultrasound emitter and at least one acoustic detector to register acoustic signals, which supplies the signals as data to a data processor. The data processor receives a plurality of acoustic amplitudes and times of flight of these amplitudes corresponding to a sample area of said meat sample. The data processor compares these amplitudes to standard amplitudes to determine the presence of bone in the sample, when bone is present, a logic signal is sent to actuate a pass-fail gate stopping the sample, otherwise no logic signal is sent. Preferably the device least one array of ultrasound emitters and at least one array of acoustic detectors to register acoustic signals, the array of acoustic detectors supplying the signals as data to a data processor. The device may comprise at least one array of ultrasound emitters above said production line and at least one array of acoustic detectors to register acoustic signals below said production line. Alternatively the device may comprise at least one array of ultrasound emitters below said production line and at least one array of acoustic detectors to register acoustic signals above said production line.

A further object is to provide a method for detecting defects in a meat sample on a production line comprising the steps of emitting at least one frequency of ultrasound onto an area of the meat sample, receiving ultrasound returned from the meat sample, measuring the amplitudes and times of flight of the returned ultrasound, comparing the amplitudes and times of flight of the returned ultrasound for each area of the meat sample by multivariate analysis, determining from said multivariate analysis the presence of surface and internal defects in said meat sample.

DESCRIPTION OF THE INVENTION

The arrangement described herein provides methods for the detection of foreign material on the surface or in the bulk of food products with a combination of spectral imaging and ultrasound measurements. Very loosely spectral imaging is used to detect foreign material proximate to the surface and ultrasound is used to detect foreign material within the sample bulk. The sample is irradiated by light and reflected light or Raman scattered light measured to give a set of amplitude data points. The sample is similarly irradiated by ultrasound and reflected sound waves give a set of amplitude data points, which include temporal delay. These spectral and acoustic data points are then processed by statistical methods to derive a set of vectors in n-dimensional space. These vectors are indicative of the presence or absence of defects. Typically the vectors indicate the presence of bone, cartilage, fat, flesh (meat or muscle in the narrow sense), or skin in the sample, and thus the presence or absence of defects.

Optical Measurements

All optical measurements are made in approximate backscatter geometry to eliminate possible shadowing effects due to irregular sample shapes. The illumination is diffuse to limit the effect of specular reflection and as homogeneous as possible. Diffuse illumination is achieved by using an extended source composed of one or more Lambertian radiators. A diffuser plate may be used to improve homogeneity. The illumination may optionally be polarized, with a polarizer rotated 90° with respect to the incident polarization positioned between the sample and detector to reduce specular reflection. The general direction of illumination is more than 150°, preferably as close to 180° as possible, allowing for spatial considerations, usually within 5°. It can be 180° if a beam splitter is used. The space between the illumination and sample may be air, but is more preferably a liquid to reduce changes in the refractive index. In another embodiment, a roller comprised of a material that transmits in the wavelength region of interest is placed in contact with the sample. The roller is cleaned to prevent the buildup of a biofilm. In all embodiments, an optical system composed of reflective and/or refractive elements is used to map radiation scattered or reflected from a small surface region of the sample with magnification onto a detector element. The linear dimensions of the small surface region are x/2 and the corresponding spatial frequency is 2/x. The Nyquist Theorem requires sampling at 2/x to resolve features with spatial frequency 1/x. Further, the optical system must transfer modulations of spectral frequency 2/x with high fidelity as determined by analysis of the modulation transfer function. The optical detector element is a photodiode, or a bolometer. A bolometer, which responds to electromagnetic radiation over a wide range of wavelengths, is less sensitive and has a slower response time. A bolometer is sensitive to air currents and is usually encased in a vacuum enclosure with an optical window. The optical characteristics of the window material determine the practical wavelength range of the bolometer.

A photodiode detector is generally a semiconductor operating on the photoelectric effect and has an effective long wavelength cut off related to the band gap. Photodiodes are more sensitive and have a faster response time, but limited wavelength range. Detector elements of either type are often grouped in arrays and each logical element in the array is called a pixel. A pixel may consist of a single or multiple detector elements. A pixel with multiple detector elements typically has an optical filter in front of each detector element to select different wavelengths. The RGB Bayer array used in color cameras is an example. A wide range of wavelength filters is available and devices with up to eight wavelength filters are commercially available. Transfer optics are placed between the sample and the pixel array to form an image of the sample on the pixel array. The required magnification of the optical system is the ratio between the pixel size and x/2. In practice the small surface region of each sample is approximately ½ mm square. The transfer optics can use refractive optics (lenses), reflective optics (mirrors) or diffractive optics (Fresnel lens). Reflective optics are achromatic. Care must be taken to select a refractive system that is corrected for chromatic aberration in the wavelength region of interest. A diffractive system can both focus and act as a wavelength filter. Other devices as known by those skilled in the art may be used instead. A wavelength selector, which may be a prism, diffraction grating, or bandpass filter, may be required to isolate and concentrate specific wavelengths, typically a range of wavelengths. When a Fourier transform spectrometer is used as wavelength selector it generally has an integral optical detector, typically a photodiode, bolometer, or an array either line scan or focal plane. Most Fourier transform spectrometers also have an auxiliary detector connection so that a detector can be located outside the spectrometer.

In calibration each pixel is illuminated with a standard light source for each wavelength and scale factors are then calculated for each pixel to equalize the response. The scale factor takes into account geometric variation in the physical size of pixel elements, as well as variation in the spectral response of each pixel element. It should be noted that the spectral response and sensitivity of a pixel is temperature dependent and a well-designed system will include a temperature sensor in close proximity to the pixel element(s) to either provide feedback to a temperature controller or to correct the scale factors for changes in temperature. Generally cryogenically cooled detectors are more sensitive. Detectors and detector arrays equipped with Peltier coolers are commercially available. Calibration is simpler for a strobed system because the same physical detector elements are used for each wavelength. The scale factor corrections for each wavelength are determined by the spectral response curve of the detector elements, which to a first approximation is the same for all of the elements in an array. The pixel array may be a single transverse array if the light emitter is strobed. It is more convenient to strobe, because of natural variation in photodiode/pixel sensitivity, and thus easier to calibrate for more reliable average amplitude. When a line scan, which is essentially one dimensional, is used, three rows of pixels, 3×1024, may be used to check for error and obtain a more reliable average amplitude. If a two-dimensional focal plane pixel array is used, typically 640×480 or 1024×1024, selected rows of pixels are used corresponding to the desired wavelengths. Again in general more than one row of pixels is used for each desired wavelength band.

In one embodiment, illumination is provided by a broadband white light source and light diffusely reflected from the sample is dispersed by wavelength by a diffraction grating or prism and position onto a focal plane array of pixels each of which register a range of wavelength.

In another embodiment, a light source with two or more types of LEDs is used and light diffusely reflected from the sample is dispersed by wavelength and position onto a focal plane array.

In another embodiment, quasi-monochromatic illumination (which could be a laser, but usually not) is provided by a LED light source in conjunction with a one or more band pass filters and resulting Raman scattered radiation is dispersed by wavelength and position on a focal plane array of pixels. It should be noted that the preferred light source is depolarized for Raman measurements because the Raman scattered intensity is polarization dependent. A LED light source generally fulfils this requirement. If a laser is used, a scrambler may be required to randomize the polarization. LEDs have a spectral FWHM of 25 to 40 nm and the required bandwidth (FWHM) is about 0.2 nm or less. A suitable filter with a 0.15 nm bandpass can be obtained from Andover Corporation, Salem N.H. The central transmitted wavelength of an interference filter can be tuned by rotating the filter and this principle can be used to construct a narrow bandpass filter from two or more wider bandpass (and less expensive) filters used in series.

In another embodiment, a laser provides quasi-monochromatic illumination and Raman scattered radiation is dispersed by wavelength and position on a focal plane array, the laser provides better spectral resolution.

In another embodiment, illumination is provided by two or more sets of LEDs that are strobed and light diffusely (not Raman) reflected by the sample is collected as a function of position by a line scan detector, which measures both wavelengths, only one wavelength is measured at a time.

In a further embodiment, InGaAs photodiodes/pixels are used to collect near infrared spectra, in the wavelength range 900 to 2600 nm. Alternately, a microbolometer array may be used. There are several suitable infrared emitters in that range as is well known to those skilled in the art. Near infrared has theoretically deeper penetration, but less sensitivity.

Embodiments that use quasi-monochromatic radiation to excite a Raman spectrum produce more independent data points than other methods described herein, that is more detailed spectra, and hence the method has greater diagnostic value. As an illustrative example, bone can be distinguished from muscle by strong Raman scattering at about 960 $cm^{-1}$ from symmetric stretching and a weaker set of bands near 1050 $cm^{-1}$ from asymmetric stretching of PO+ in hydroxyapatite. Lipids can be determined from the symmetric and asymmetric C—H stretching bands in the region between 2850 $cm^{-1}$ and 3050 $cm^{-1}$. Proteins produce a distinct Raman spectrum, which includes information about protein secondary structure. The most important protein feature is the Amide I band near 1650 $cm^{-1}$ of amino acid residues in peptides. For these measurements, the exciting wavelength should be chosen as the shortest wavelength that does not cause a significant rise in the fluorescence background. The intensity of Raman scattering is proportional to the fourth power of the incident frequency. Fluorescence can be avoided by use of near infrared incident light at the cost of lower signal levels. A suitable wavelength is 633 nm, which can be provided by either a LED or a HeNe laser, which avoid fluorescence. A lens system typically used to collect radiation scattered from the sample and transmit said radiation to a wavelength selector. The wavelength selector must prevent radiation at and near the incident wavelength from reaching the detector element(s) as the power at the incident wavelength is typically a factor of a million higher than the power at the measurement wavelengths. The incident wavelength can be blocked by an interference filter or by a double (or triple) grating system. Both options are commercially available from many vendors and there are a number of commercially available laser LEDs have wavelengths in the visible and near infrared, which are suitable, for Raman excitation, including 488, 515, 532, 594, 635, 650, 660, 610, 785, 808, 830, 850, 980, and 1064 nm. In practice the operating wavelengths may differ from the nominal wavelengths by about 5 nm due to variations in operating conditions. The detector is chosen for sensitivity at the Raman scattered photon wavelength range. An array of avalanche photodiodes is the preferred detector technology as the sensitivity is in the fW to pW range, which compares favorably with a Raman signal in the nW range. A photomultiplier tube will also work if the excitation wavelength is less than 600 nm. CCD technology will also work, but longer sampling times (or higher input power) are needed due to lower sensitivity. Cartilage, like muscle is composed of a sequence of amino acids, but has an atypical distribution of amino acids. In cartilage approximately ⅓ of the amino acid residues are proline. A resonance Raman spectrum selectively sensitive to proline can be excited with radiation between 200 nm and 220 nm. Fluorescence is a problem with UV excitation. Where fluorescence is unavoidable, it is possible to collect a Raman spectrum with a pulsed light source coupled with time-gated detection to reject fluorescence, which arrives at a larger time delay than the Raman signal, typically about 200 ns. The detector is turned off after Raman detection, to allow fluorescence to pass, then it is switched on again for the next Raman detection. The output light is passed through a device, usually a diffraction grating, (in theory a prism can be used), and its intensity measured on a pixel array, alternatively a Fourier transform spectrometer may be used, which may be combined with a line scan detector, or focal plane array.

To determine the most effective wavelengths, samples of chicken were tested over a range of 400 to 800 nm, in discrete 10 nm bands and the reflected amplitude measured for each band. The amplitude was measured compared to the standard deviation. The samples approximated 700 by 700 pixels although the camera was 1024 by 1024 pixels. Areas of cartilage, bone, skin, fat and muscle were identified and masks covering only unambiguously determined surfaces were used to provide amplitudes of reflected light for the pixels within the mask for each type of surface, which numbered from at least a thousands pixels up to twenty thousand to provide reliable average amplitudes and standard deviations. Ranges of 540 to 570 nm, 620 to 640 nm and 720 to 760 nm were found most effective. All three ranges are needed, each with a significant contribution to eigenvectors which explains variance in sample. As noted below, eigenvectors are derived sufficient to identify the nature of the surface.

For embodiments that use reflected light, an instructive example is provided by describing the application of the invention to the problem of finding defects on poultry breasts. In one embodiment, Si based photodiodes are used. The spectral responses of a chicken rib and chicken breast muscle are statistically indistinguishable in the region around 630 nm and this property makes 630 nm a good normalization reference. In the spectral region proximate to 720 nm, the means of the chicken rib and chicken breast distributions are separated by the sum of their standard deviations. Hence measurements at 630 nm and 720 nm are sufficient to distinguish between chicken rib and chicken breast muscle. Cartilage is more reflective than bone. At 630 nm and 720 nm, the ratio is about 1.1 whereas at 570 nm the ratio is about 1.8. Hence cartilage is inferred by higher reflectivity at 570 nm and similar reflectivity at 720 nm relative to the 630 nm reference measurement. At 570 nm, chicken fat is about 3.4 times more reflective than muscle relative to the 630 nm reference. Skin approximates to fat for spectral reflectivity. At 720 nm, fat is less reflective than muscle (0.84) relative to the 630 nm reference. These wavelengths were determined by experiment to be effective and to form a sufficient basis set for multivariate analysis. The three amplitudes are determined for each pixel. In practice the three amplitudes for each pixel are subjected to multivariate analysis to derive projections onto eigenvectors in n-dimensional space, which are then used to determine the nature of the sampled surface area.

While 570, 630 and 720 nm, are preferably strobed, they don't have to be. LEDs warm up is fast on the order of microseconds, however the shutdown is slow on the order of 300 microseconds. Consequently a delay of about 300 microseconds is required between the time a LED is turned off and the beginning of the next integration period. Strobing generally requires that each LED or group of LEDs of the same wavelength has its power converter controlled by a switching circuit, such as an H bridge in combination with a current limiter, a LED driver or similar logic processor. A BuckPuck (LED Supply, Randolph Vt.) is a suitable control device.

Recently conveyor belts carrying meat samples have speeded up to around 15,000 samples per hour, or about 4 per second corresponding to a line speed of 1600 mm/s. To make 3 measurements per 0.5 mm of translation the required sampling frequency is 9.6 kHz for a linear array, which is problematic considering the LED turn off time noted above. Our experiments were done on a line running at 800 mm/s, so the required sampling rate for a linear array is 4.8 kHz. A two dimensional focal plane array can be used instead to record multiple images of the same sample region at different times. All that is required is that the sample translates by less than 0.5 mm during the integration time (0.625 ms in our case). Thus a series of overlapping 2-D images are collected for each wavelength. The images have to be offset by the relative movement between images, so as to provide a single 2-D image for each sample for each wavelength. This may be done two ways. The integration time is set according to the desired Nyquist spatial resolution as described previously. It is possible to measure all wavelengths with one focal plane array detector in sequence. The integration time which is the time the detector is switched on to receive photons and sum their energy is typically about ¼ to ¾ millisecond. The focal plane is for example 1360 pixels transverse by 1024 long, for example an area of about 640 pixels transverse by 240 long is used as a frame, essentially a single picture. The frames are taken at different times, as there are three separate wavelengths. The period between frames is usually larger than the integration time due to the time needed to transmit sensor data to the data processor. During the period between frames, the sample will have translated a distance X mm corresponding to preferably 2X pixels. The value of X and the pixel displacement are calculated from the translation rate of the sample. The interval is typically 21/2 milliseconds. As the sample passes under the camera a series of frames are taken at each wavelength, one cycle takes 71/2 milliseconds, in practice corresponding to about 12 pixels. The amplitudes of a particular transverse row of pixels in one frame is compared to rows 11, 12, or 13 in the next frame of the same wavelength, in general one of these is identified as the same, that is shown to be identical. If the sample is used, the dot product between a region of a first image and a subsequent image (with a range of offsets) is calculated and normalized by the magnitude of each data vector. The offset that produces a value closest to 1.000 is used. The frames or rather the pixel amplitudes corresponding to a common small sample region after appropriate offsets are summed to give longer effective integration. While up to 20 frames may be used in the example given, the general method can be extended to an arbitrary number of frames by using multiple focal plane arrays with fields of view offset by known displacements. The summed amplitudes increase with the number of frames and the noise increases as the square root of the number of frames giving an overall improvement in the signal to noise ratio proportional to the square root of the number of frames co-added. This amplification method is particularly useful for Raman measurements with intrinsically weak signals. The raw pixel amplitudes are normalized at each wavelength by a scale factor to normalize the response to a white reference. These amplitudes produce a three dimensional vector, which is used to characterize the nature of the surface of the sample.

Encoder marks may be included on the sample transport substrate (conveyor belt) for the purpose of calculating pixel offsets. These marks are equi-spaced distinct markings which can be used to coincide the images from each frame, the markings will have the same positional relationship to each sample, which can then be identified. Pixel values for the same sample region are added for each wavelength. It is also possible to measure all wavelengths simultaneously using separate detectors with the use of one or more beamsplitters. As three sets of focal planes comprising pixels each for a separate wavelength are used, the normalization is more complex as it has to take into account all the pixels at all three wavelengths. In this case, the period between measurements is reduced, but care must be taken to align the detectors to a common field of view. In either case, it is possible to record multiple images of each sample region increasing the effective integration time and improving the resultant signal-to-noise ratio. As an illustrative example, a camera with a 1280×1024 pixel focal plane array may be used and the sample is translated in the Y direction. The sample translates 256 pixels in the period between measurements at the same wavelength. In this example each physical region is measured 4 times. The data processing time is a function of the number of bytes and the speed of the processor.

Preferably the optical system is enclosed in a chamber shielded from ambient light, including the effect of 60 Hz fluorescent lighting. Modulating the amplitude of illumination and passing the modulation signal to a lock-in amplifier linked with the detector outputs can eliminate the effect of ambient light.

Acoustic Measurements

The invention further includes an array of ultrasound transducers arranged to span the width of a sample conveying apparatus such that every region of the sample zone can be scanned. The walls of the sampling region are coated with a material designed to absorb and damp ultrasonic vibrations. For example, the array may be approximately 210 mm across to match the width of the conveyor system used in the optical example. Other sizes are possible and should be chosen to approximately match the size of a particular conveyor system. Three variants are envisaged. The first couples acoustic vibrations to the sample through an aqueous medium. In this case back reflection geometry is preferred. In the second variant samples are positioned on one side of a conveyor belt and at least one transducer is coupled via a liquid to the opposite side of the conveyor belt. The acoustic signal is transmitted through the conveyor belt, through the sample and travels through an air gap before being received by at least one transducer. The positions of the transmitter and receiver may by interchanged. The third couples acoustic vibrations to the sample through a roller. In this case one or more transducers are mounted in the roller. The transducer(s) may rotate with the roller, but more preferably are stationary positioned near the center and couple with the moving surface of the roller through a liquid.

In one embodiment, a line of transducers preferably 6 mm in diameter is used, usually having around 32 transducers, which are sufficient to span a typical chicken breast. The 6 mm transducer is large enough to produce a well-focused ultrasonic wave, yet small enough to keep the return from a defect as small as 0.3 mm within detection limits. The noise/signal ratio for this size is calculated theoretically. The transducers may resonate between 1 MHz and 20 MHz, most preferably 5 MHz in aqueous medium. In air a suitable frequency is 200 KHz. Higher frequency gives better resolution and lower penetration depth. The ultrasonic frequency is chosen such that the ultrasonic wavelength is smaller than the minimum defect size x and most preferably smaller than x/2. In this limit, structures with dimensions x and larger generate an acoustic dipole field that can be observed in the backscatter geometry. When the acoustic signal is reflected it has a number of lobes, which vary with situation, both forward and backscatter lobes are always present. The backscatter geometry is used in the present invention in preference to the forward scatter geometry because the weak scattered signal is not combined with the strong incident wave, as is the case in the forward scatter geometry. It is worthwhile to note that particular defect geometries where the defect is about the same size as the ultrasonic wavelength can produce reflected waves that are a strong function of scattering angle with strong signals at some angles and no signal at other angles. The backscattering geometry does not produce the strongest possible signal in these cases, but it does produce a consistent signal, which is preferable to the possibility of a missed signal. The backscatter geometry allows the same transducer to both send and receive ultrasonic waves, provided that the oscillation from generating the outgoing pulse dampens to negligible levels prior to the arrival of scattered waves.

In an alternative embodiment, a separate set of transducers can be positioned in close angular proximity but acoustically insulated from the first set of transducers to function as receivers. The detectors measure the effective acoustic conductance or impedance of the tested material, and thus indicate its density, differences indicating bone, cartilage, fat and muscle. In this embodiment the transducers may all emit at once, and measure the acoustic response simultaneously. They also may emit with a time phased lag, which can sweep the sample in microseconds. The width of the sample channel may be divided into N regions. The time required to sample each region is approximately the time required for an ultrasound wave to travel from the transducer to the bottom of the sample conveyor and back. The transducer set/phased array sends a short focused acoustic wave train separately into each region, starting with region 1 and ending with region N in sequence until a complete line across the sample region has been interrogated. The process repeats indefinitely. During the sampling time, backscattered waves are sampled at twice the frequency of the incident waveform. For example, the time required for a return trip for a 5 MHz wave train through 20 mm of soft tissue is about 28 microseconds, consequently about 280 data points are needed to characterize the backscattered waveform. In another embodiment, more than one region can be sampled at the same time, provided that the regions are far enough apart to avoid cross-talk. As a result of the phase difference there is destructive interference except within a small sample region. Essentially one response is received from one area of the sample at a time.

In the air embodiment the transducers may all emit at once, and the detectors measure the acoustic response simultaneously with each other. They also may emit with a time phased lag, which can sweep the sample in microseconds. The width of the sample channel may be divided into N regions. The time required to sample each region is approximately the time required for an ultrasound wave to travel from the transducer to the receivers at the bottom of the sample conveyor. The transducer set/phased array sends a short focused acoustic wave train separately into each region, starting with region I and ending with region N in sequence until a complete line across the sample region has been interrogated. The process repeats indefinitely. For example, the time required for the passage for a 200 KHz wave train through 20 mm of soft tissue is about 14 microseconds, in the example shown. In another embodiment, more than one region can be sampled at the same time, provided that the regions are far enough apart to avoid cross-talk. As a result of the phase difference there is destructive interference except within a small sample region. Essentially one response is received from one area of the sample at a time. The transmitters may be above and the receivers below the production line or the transmitters may be beneath and the receivers above the production line.

A larger number of transducers may be used, typically 64 or 128, in a phased array of the same physical size, this set up is similar to medical ultrasound applications and has similar resolution and sensitivity.

In another embodiment, the amplitude, phase, or frequency of the outgoing wave train can be modulated to encode temporal information. When the transducer array is in time phased lag, each transducer has its power converter controlled by a switching circuit, such as an H bridge, or similar logic processor.

Data Processing

The signals from spectral measurements and ultrasound measurements are transmitted to a data processing apparatus, which uses conventional statistical models to infer the presence or absence of a defect. The supplied information includes the amplitude at specific wavelengths from the detector(s), acoustic amplitude(s) together with time of flight.

The optical amplitudes can be used as absolute values, when subjected to multivariate analysis. It is preferred that the optical amplitudes are mean centered, and normalized to standard deviation. If the amplitude is below a certain threshold (that is there is no portion of the sample present) it is not processed. The mean of amplitudes for the sample is taken for five transverse scans; this number can be varied in practice, depending on the detector. This mean is then subtracted from the amplitudes of the current scan to give mean centred amplitudes. The standard deviation for that scan is then calculated and the mean centred amplitude divided by the standard deviation to give a mean centred normalized amplitude. This takes account of height difference in the sample. The mean centred normalized amplitude a' is given by the expression $a'=(a-m)/s$, where a is the measured amplitude m is the mean and s the standard deviation. The edge amplitudes are identified by the data processor for the eight adjacent areas, to the tested area, abutting directly and diagonally. In theory these are then compared for gradient from tested central amplitude to adjacent peripheral amplitudes to detect the presence of an edge and hence bone, when the gradient is greater than standard by a noise threshold.

In the aqueous case, while there is one spectral amplitude at each wavelength for each area, there is more than one acoustic amplitude for each area. In practice the acoustic amplitude is plotted against time of flight whichever transducer embodiment is used, there are five possible outcomes. First, the ultrasonic wave may be emitted into a region with no sample and simply reflect with attenuation off the opposite face of the sampling region. Secondly, the ultrasonic wave may encounter a sample region with a quasi-homogeneous acoustic impedance. In this case there will be a backscattered wave from the top surface of the sample, weak scattering by the sample bulk, another backscattered wave from the bottom surface of the sample, and finally scattering from the bottom surface of the sample channel. The third case is the same as case 2, except that a small particle on the top surface with higher acoustic impedance than the bulk increases the amplitude of the wave scattered from top surface. Case 4 is the same as case 3, except that the small high impedance particle is on the bottom surface and increases the amplitude of that reflection. In cases 3 and 4, the increased scattering is used together with optical data to determine the presence of a defect. Case 5 is the same as case 2, except that a high impedance particle is between the top surface and bottom surface. In this case there is an extra scattering signal at a time intermediate between reception of the top surface and bottom surface signals. In the non-aqueous case the presence of bone changes the time of arrival of the transmitted wave as the speed of sound is faster in bone.

Multivariate analysis such as Principal Component Analysis (PCA), Neural Networks (NN), Linear Discriminant Analysis (LDA), Partial Least Squares (PLS) and similar algorithms can all be used to infer the probability that a bone fragment is present. Two general methods are used to infer the presence of a defect from optical measurements. Firstly, it is possible to assign a probability that a defect exists within an individual pixel based on differences in the signal received as a function of wavelength. Secondly, the probability of a defect in a region corresponding to a pixel can be calculated by comparing the pixel to surrounding pixels to detect edges. Edge(s) imply the presence of bone. This detection is done with a direct gradient calculation, use of a Sobel mask, or other edge detection algorithm, which compare adjacent amplitudes to derive a rate of change (gradient) of amplitude. A larger gradient corresponds to a higher edge and defect probability. In practice the eight neighboring amplitudes for each wavelength are combined with the central amplitude to generate an edge probability amplitude for each wavelength. The edge probability amplitudes are included in the data vector used to calculate eigenvectors for calibration or eigenvector projections for operation. The ultrasonic signal as a function of time relative to a reference point is included in the data vector. The pattern produced by an included bone is different, but difficult to model with a direct physical model. The statistical model calculates the cumulative probability that a defect exists within a small sample volume based on all of the measurements. Specifically, the wavelength dependence, the edge probability, and the acoustic return as a function of time relative to a surface reflection are loaded into a common data vector and the projection of this data vector onto a set of orthogonal calibration vectors is calculated. Preferably, but not necessarily, the data is mean centred and normalized by the standard deviation of each measurement. For illustrative purposes the general method for implementing a PCA (Principal Component Analysis) is outlined herein. In the PCA method, the set of reference vectors are eigenvectors, which each describe a Principal Component n-dimensional space. A set of eigenvectors and eigenvalues are generated from a calibration set of data vectors by a multivariate analysis (PCA) routine. The data vectors in the reference set represent a set of samples with bone fragments and a set of samples without bone fragments. The number of samples in each set is chosen such that the natural variability within each population is well represented. The covariance matrix is calculated and the eigenvectors and eigenvalues are obtained by diagonalizing the covariance matrix. If the data vector is of dimension m, there will be m eigenvectors and m eigenvalues. If 3 wavelengths are measured there are 3 amplitudes plus 24 edges and m=27, more if acoustic measurements are included. All of the eigenvectors corresponding to unique eigenvalues are orthogonal. Degenerate eigenvalues are possible, in which case any one of 2 or more degenerate eigenvectors is used to represent the eigenvalue. The sample variance described by each eigenvector is proportional to the magnitude of the associated eigenvalue. Usually >99% of the variance is described by the largest 2 to 6 eigenvectors which are called PC1, PC2, PC3, etc. in order from largest to smallest corresponding eigenvalue. The sample variance can be projected into a reduced dimension vector PC space by taking the dot product of each data vector with each of the 2 to 6 eigenvectors corresponding to the largest eigenvalues. The dot product gives the projection of the original data vector along each principal component eigenvector. The new vector space is n-dimensional (n usually less than 6 and most often about 3) and all of the vectors are orthogonal. If the original data vector is mean centred and normalized by the standard deviation, the units of the eigenvectors are standard deviations and this is convenient (but not necessary) for interpretation of the data in the PC space. Calibration vectors corresponding to skin, bone, muscle, fat, cartilage, etc. cluster in different regions of the PC space. The locus of each tissue type distribution, together with probability at increasing distance from the locus is modeled. When the system is presented with an unknown, the data vector is projected into PC space and compared with the model for each tissue type to generate a probability for each tissue type. The diagnosis for the sample region is the tissue type with the highest probability. Data vectors in the calibration set with bone fragments project onto a different region of Principal Component space from data vectors in the calibration set without bone fragments. Although some variation in data vectors is noted in practice they fall into quite distinct groups with little ambiguity. Principal component plots are available but require different colors for clear interpretation.

Standard samples of bone, cartilage, fat, flesh, and skin are used to calibrate the eigenvectors. In general a contaminant does not correspond to any calibration set, and stands out. Standard Bayesian statistical methods are used to calculate the probability that a bone fragment is present for each small region of Principal Component space. The projection of an arbitrary data vector into Principal Component space determines the probability that the data vector represents a bone fragment defect. If the calculated probability exceeds a threshold, a signal is produced by the logic system that can be used to remove the defective piece from the process stream. The defective piece can optionally be re-worked, via a trim line, and then re-inspected. Other wavelengths and algorithms could arrive at the same end result.

The advantage of the system is that it detects both surface and embedded bone in chicken breast. Although the surface of a food sample may be quite irregular on a large scale, the surface normally does not vary much on a scale of a few millimeters so the illumination and mean angle of reflection are nearly constant. Within this approximation, 94 Edge detection is well known, and off the shelf processing software is commercially available. Once an edge is detected, the algorithm searches for other nearby edges and calculates a defect probability based on the magnitude of the gradient, the length of the edge, and the mutual geometry all edges within an analysis region. As an illustrative example, bones often have edges that are nearly parallel with a characteristic spacing between edges. The detection of parallel edges several mm long approximately 2 mm apart in chicken flesh would cause the algorithm to generate a high probability for the presence of a chicken rib.

The products to be inspected may be in air. In this instance, a disposable transparent film separates the optics from the sample area. The film may be slowly scrolled between two rollers at a rate that maintains a clear field of view between the sample and detector. It is understood that an optical inspection apparatus can be positioned to face each surface of the sample. In a preferred embodiment, one set of optical detectors faces the top surface of a sample and a second set of optical detectors faces the bottom surface. Preferably, the sample is immersed in a clear liquid solution, which minimizes or eliminates specular reflectance, during optical scanning and also couples acoustic waves into the sample more effectively than an air interface. The clear liquid solution may be primarily water. In this embodiment, a submerged clear window separates the optics from the sample. The clear window is preferably recessed to prevent abrasion and cleaned periodically to prevent the accumulation of a biofilm.

DESCRIPTION OF THE PREFERRED EMBODIMENT

Figure 1:
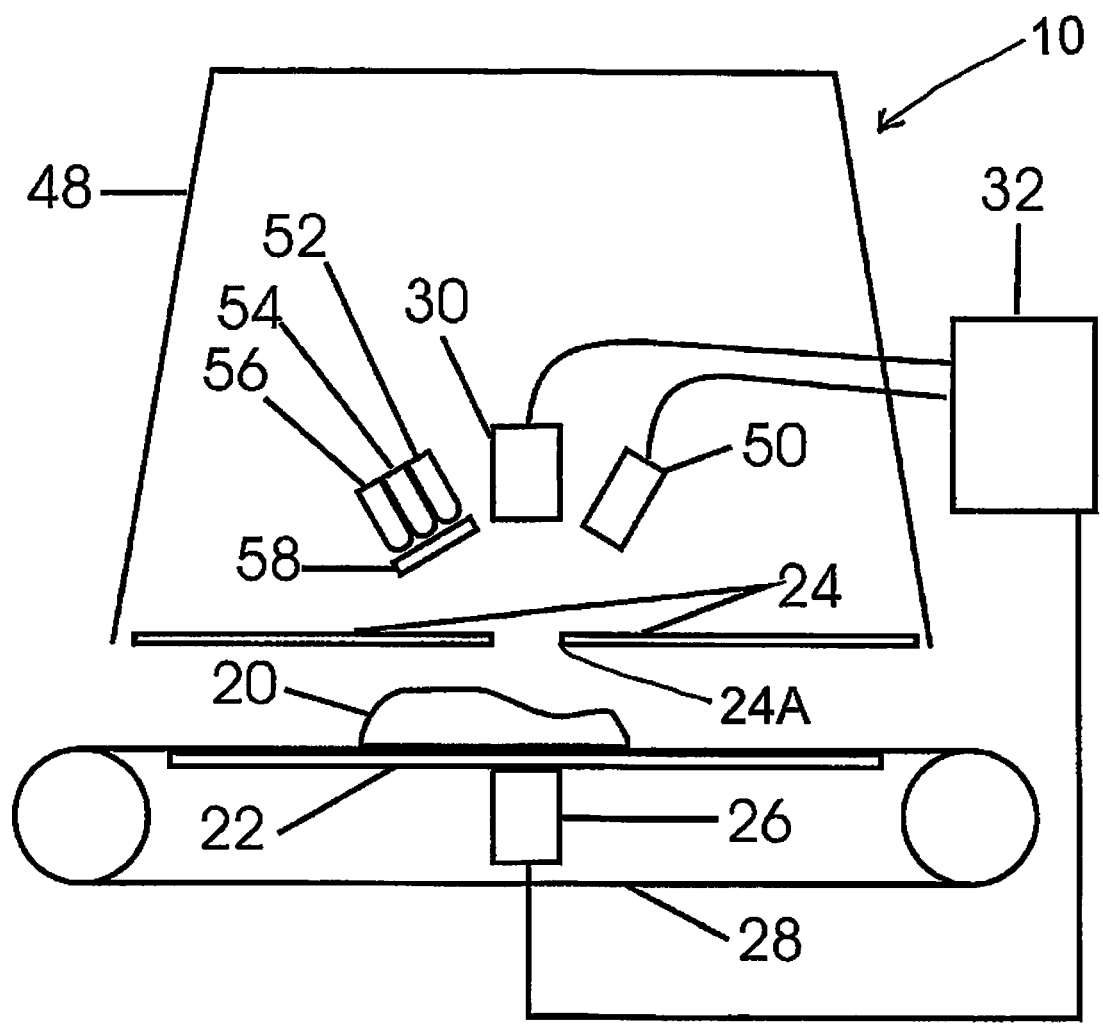
FIG. 1 shows a schematic side elevational view of a first method according to the present invention.

In FIG. 1 an apparatus 10 is provided where a meat sample 20 is carried on a conveyor belt 28 an upper supporting run of which is carried on a metal plate 22. An acoustic transducer 26 driven by an electronic control 32 is rigidly mounted to the metal plate 22 and acoustically coupled with grease (not shown). The metal plate 22 is acoustically coupled with the conveyor belt 28 with a thin layer of an aqueous solution (not shown). The conveyor belt 28 is acoustically coupled with a meat sample 20 carried on the belt with a thin layer of the aqueous solution (not shown). An aperture 24A is provided in a plate 24 which allows transmission of signals emitted by the transducer 26 and transmitted through the sample 20 to an acoustic transducer 30. The plate 24 prevents indirect acoustic disturbances (echo) from impinging on the transducer 30. Signals received by the transducer 30 are transferred to and amplified by the electronic control 32. An enclosure 48 surrounds the system 10 and prevents ambient light from entering the apparatus 10.

Illumination of the sample 20 on the conveyor 28 is effected by LEDs 52, 54 and 56. LED 52 is 570 nm, LED 54 is 630 nm and LED 56 is 720 nm. A diffuser 58 is located in front of the LEDs and provides uniform illumination. LEDs 52, 54 and 56 are strobed and reflected images at each wavelength are collected by a camera 50 and transmitted to the electronic control 32. Acoustic and optical signals are combined in a data vector and analyzed for presence of bone fragment by the electronic control 32.

Figure 1A:
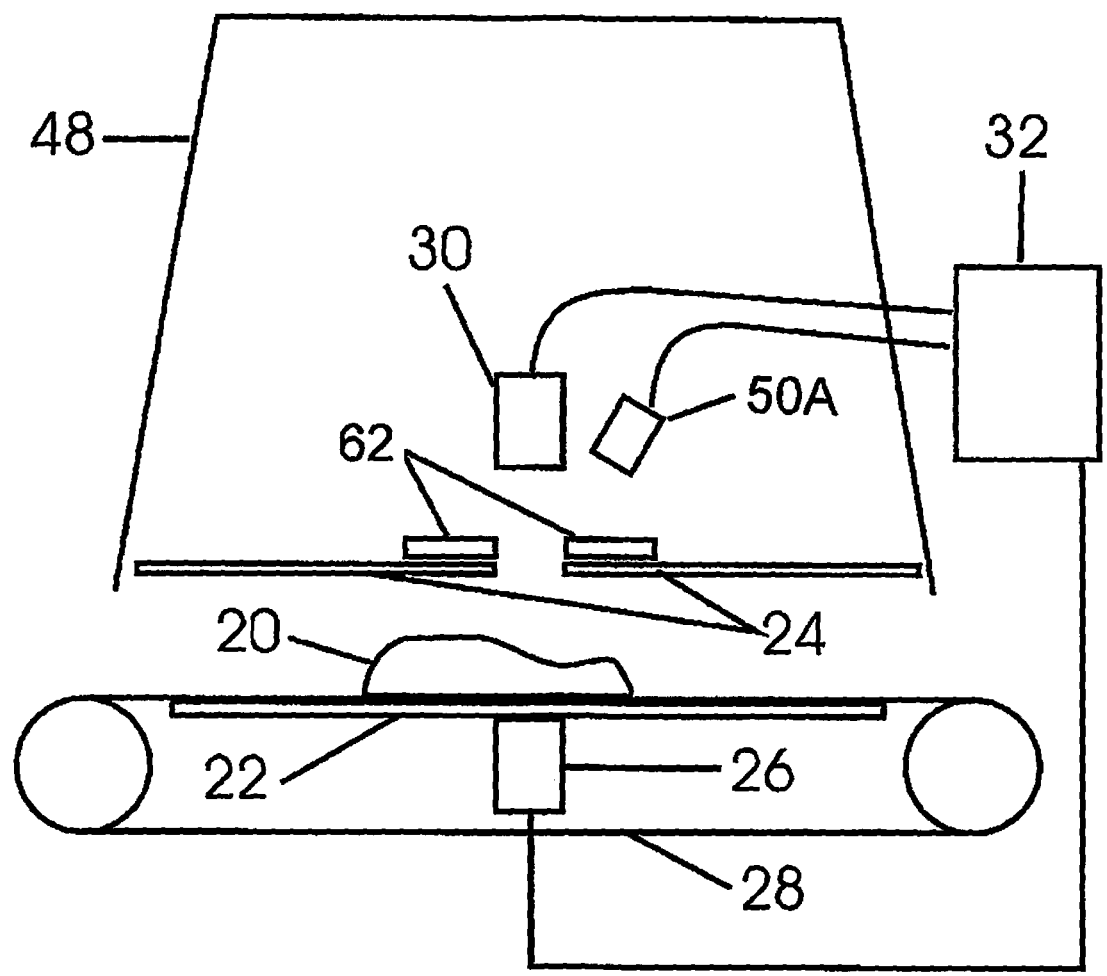
FIG. 1A shows a schematic side elevational view of a second method according to the present invention similar to that of FIG. 1.

In FIG. 1A is shown an apparatus similar to FIG. 1. In this embodiment, the aperture 24 is transparent to near infrared radiation and a broadband near infrared source 62 illuminates the meat sample 20. A spectral camera 50A forms image of reflected near infrared radiation in a first plane containing a slit (not shown) to select a sample region approximately 0.5 mm wide. Near infrared radiation passing through the slit is collimated and is dispersed by a grating or prism (not shown) and is imaged onto a InGaAs or microbolometer array. The spectral data is transmitted to the electronic control 32. Acoustic and optical signals are combined in a data vector and analyzed for presence of bone fragment by the electronic control 32.

Figure 1B:
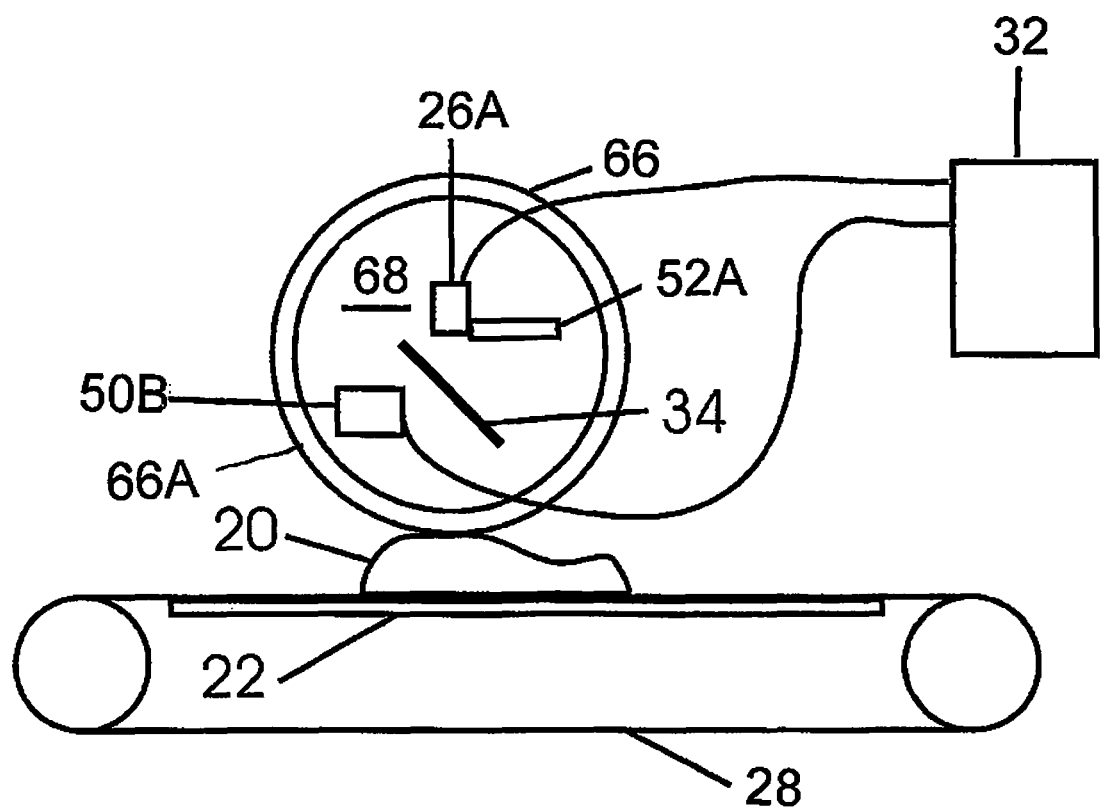
FIG. 1B shows a schematic side elevational view of a third method according to the present invention similar to that of FIG. 1.

In FIG. 1B is shown a further similar embodiment where the meat sample 20 is carried on a conveyor belt 28 supported by the metal plate 22. In this embodiment a roller 66 is mounted on a suspension system (not shown) which keeps an outer cylindrical surface 66A of the roller in contact with and applies pressure to the meat sample 20. The roller 66 is filled with liquid 68 which provides acoustic and optical coupling between the roller 66 and a transducer 26A inside the roller 66. Also a light source 52A, beam splitter 34 and camera 50B are located in the roller 66 so that the illumination from the source 52A is directed through the splitter 34 and through the transparent wall 66A with reflected light passing along the same path to the splitter 34 which is angled to direct the reflected light to the camera 50B. Acoustic and optical signals are combined in a data vector and analyzed by the control system 32 for presence of bone fragment by electronic control 38.

Figure 1C:
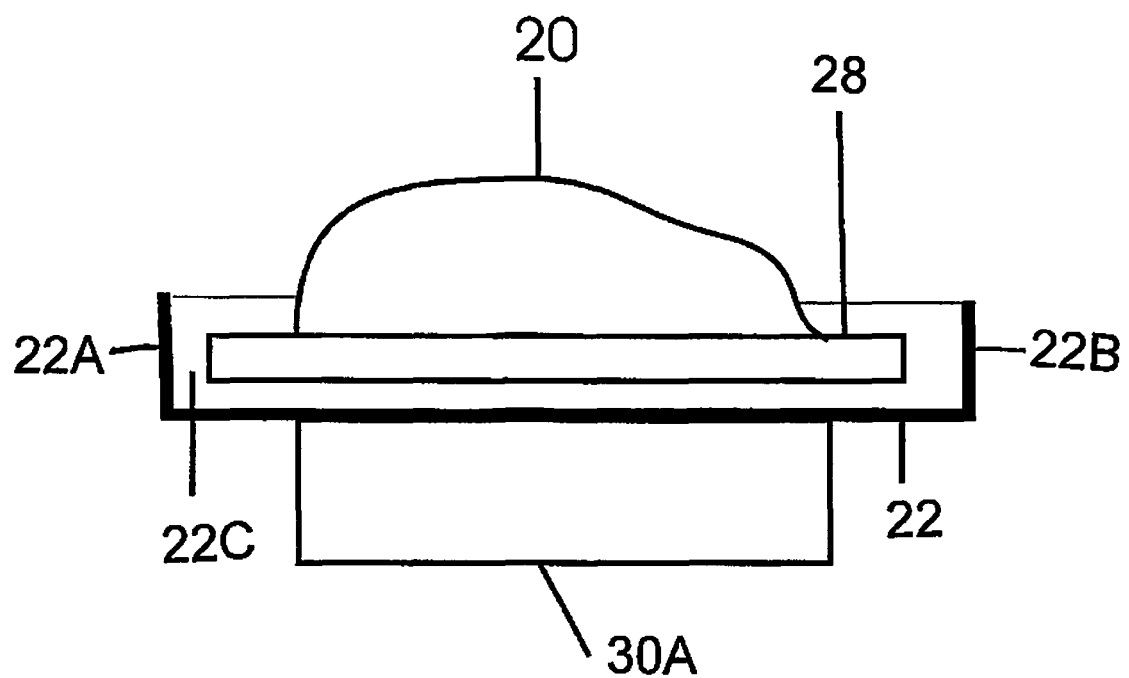
FIG. 1C shows a schematic side elevational view of a fourth method according to the present invention similar to that of FIG. 1.

In FIG. 1C is shown a further similar embodiment in cross sectional view where a meat sample 20 rests on the conveyor belt 28. The metal plate 22 has upturned edges to retain an aqueous solution 22C. A transducer array 30A is mounted on the metal plate 22.

Figure 2:
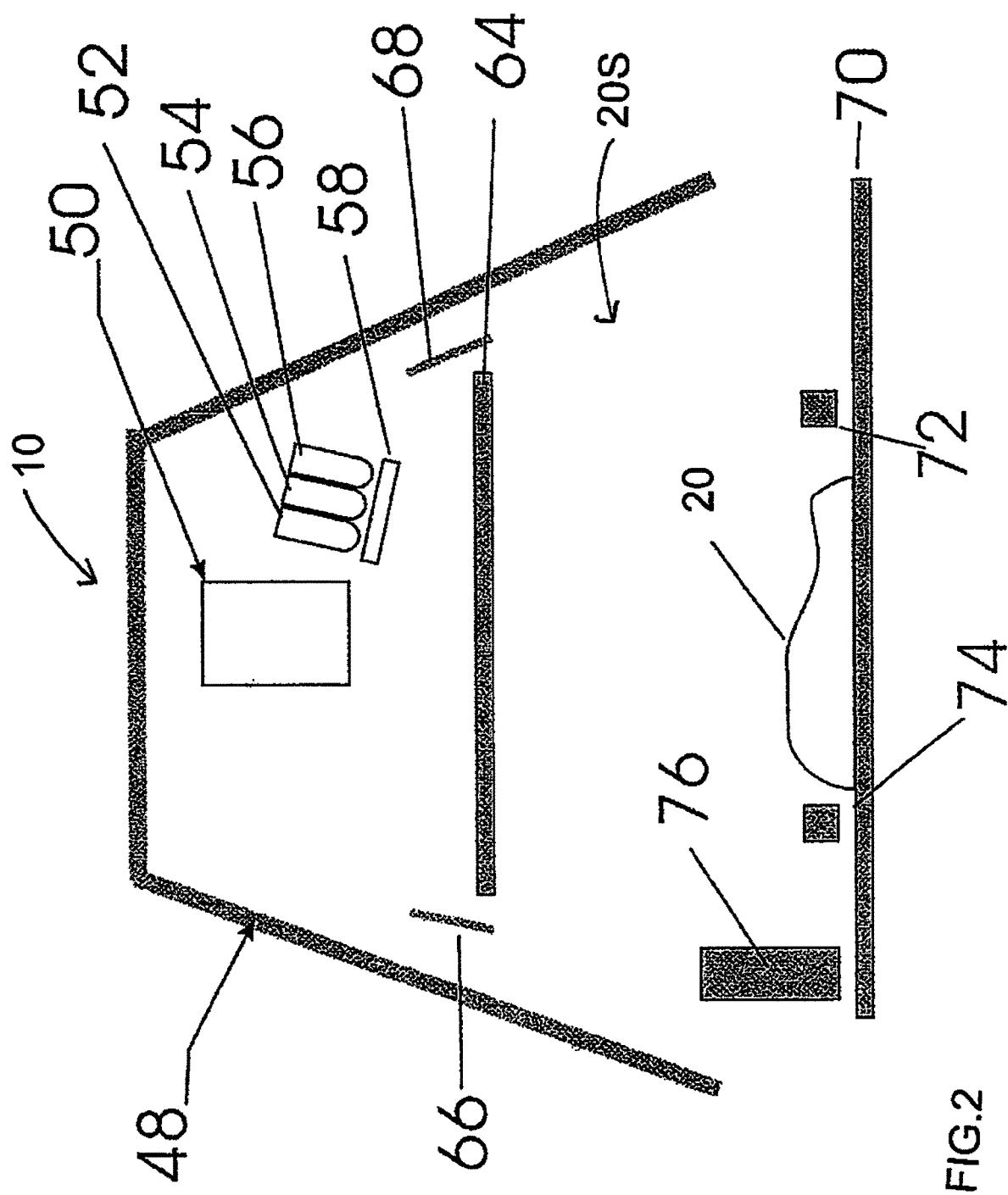
FIG. 2 shows a schematic side elevational view of a further method according to the present invention.

In FIG. 2 is shown a further similar embodiment where the detection device 10 has an enclosure 48, camera 50, LEDs 52, 54 and 56. LED 52 is 570 nm, optional LED 54 is 630 nm, and LED 56 is 720 nm. The LEDs have an associated diffuser 58 located above a cover plate 64. Air purgers 66 and 68 remove heated air from the device 10 within the enclosure 48. Below the device 10 in the sample space 20S is conveyor belt 70, motion control sensors 72 and 74 and pass/fail gate 76. Also shown is chicken sample 20.

Figure 3:
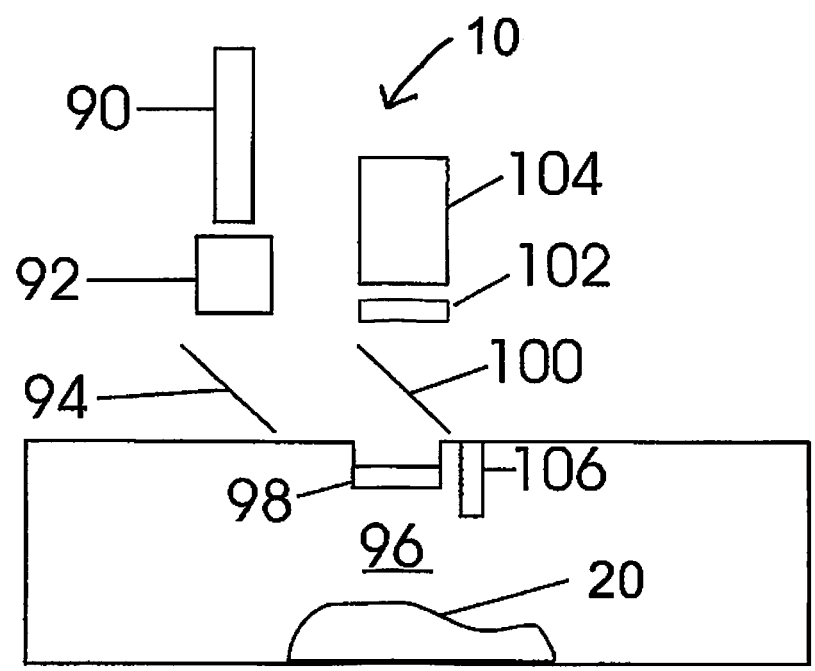
FIG. 3 shows a diagrammatic side elevation view of another embodiment of the device.

In some cases only 570 and 720 nm LEDs are employed. This system generates reflected amplitude, of very strong reflectivity for bone, cartilage, fat, skin, meat/muscle, and membrane. Submersion eliminates specular reflection. Several samples were run to ascertain effective reflectance. The presence of the third optional 630 nm LED can provide an enhanced detection. Visual comparison of samples to computerized results from the dual LED setup compared were not as a satisfactory as comparison to computerized results from the triple LED setup. Normalization using 630 nm produced better results In FIG. 3 is shown another embodiment of the device 10, in which a laser 90 supplies light through linescan generator 92, which transforms a circular laser beam, into a transverse linear beam, or a set of transverse linear beams. A steering mirror 94 diverts the beam to a beam splitter 100 which sends the beam through a window 98 to the chicken sample 20 immersed in water or aqueous fluid 96. The window 98 is recessed below the water level of the fluid 96 to avoid bubbles. Reflected Raman scattered light is passed back through the window 98, beam splitter 100 and filter 102 to Fourier transform spectrometer 104 for amplitude measurement. Filter 102 is chosen to reject light at the wavelength of the laser 90. Acoustic transducer 106 both emits and receives ultrasound.

Figure 3A:
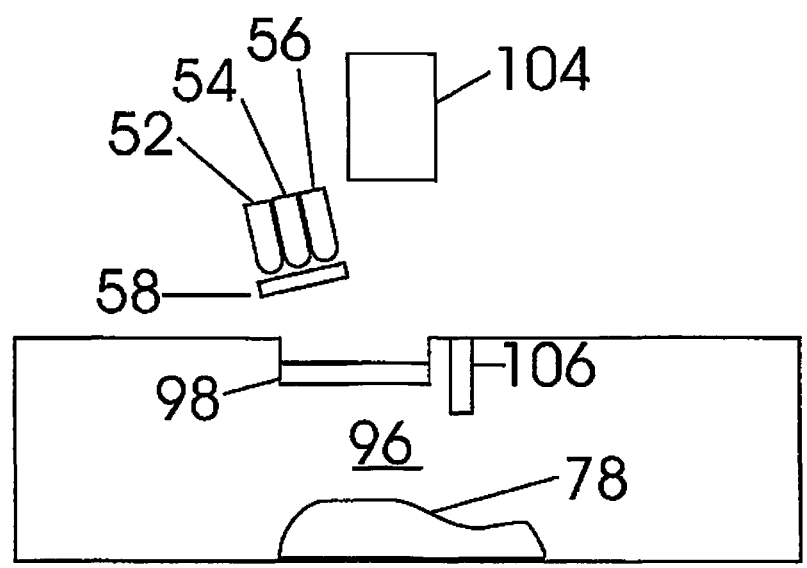
FIG. 3A shows a diagrammatic side elevation view of another embodiment of the device.

In FIG. 3A is shown another embodiment of device 10 similar to that of FIG. 3, in which chicken sample 20 is immersed in aqueous fluid 96. The sample is illuminated through the window 98 in sequence by LED 52 (570 nm), LED 54 (630 nm) and LED 56 (720 nm). Incident light is homogenized by the diffuser 58 and passes through the window 98. Reflected light is passed back through the window 98, and imaged by camera 104 for amplitude measurement. Acoustic transducer 106 both emits and receives ultrasound.

Figure 4:
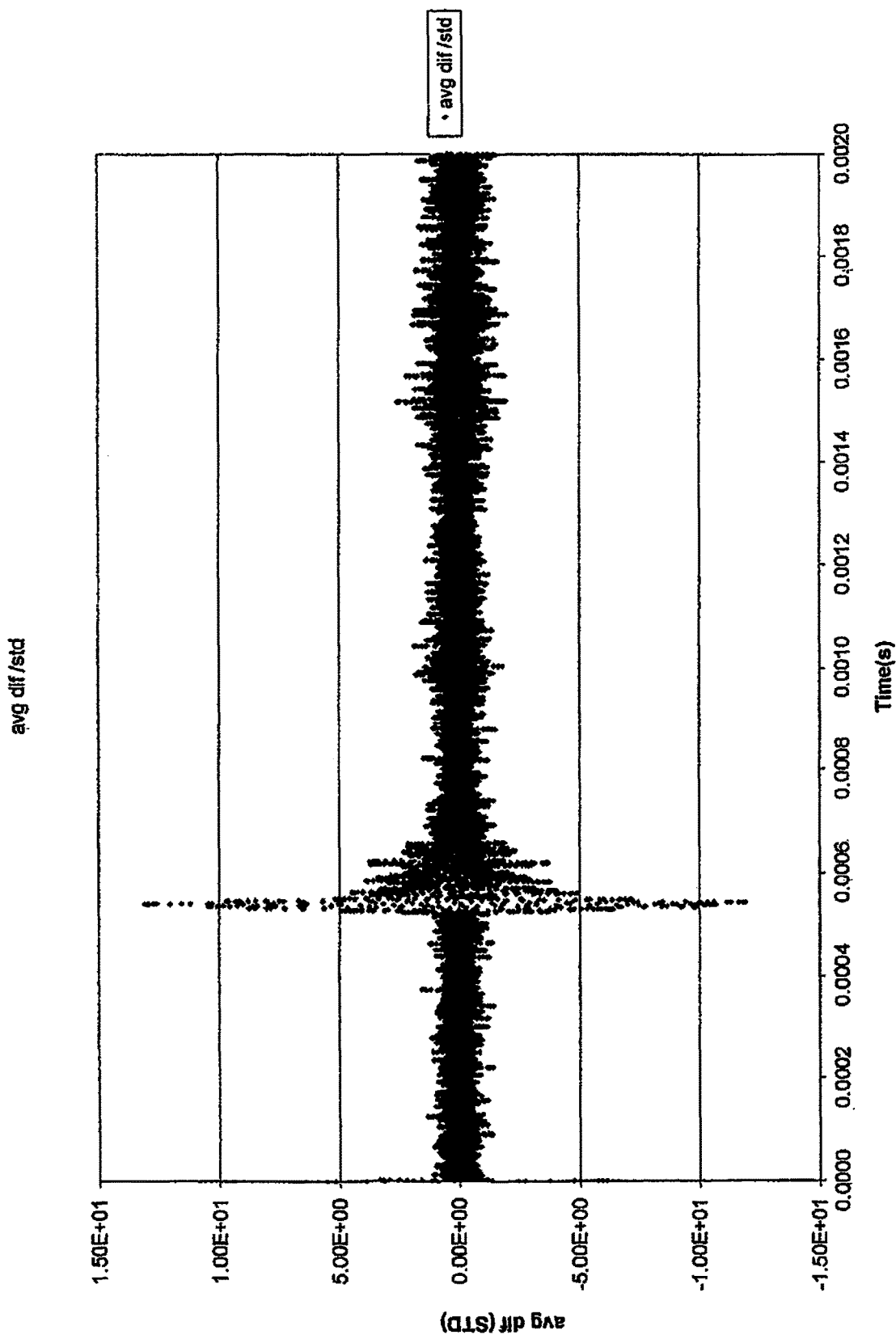
FIG. 4 shows a plot of amplitude measured as amplitude/standard deviation against time in milliseconds.

In FIG. 4 a plot of amplitude measured in standard deviations against time in milliseconds is shown. The strong response around 50 microseconds indicates bone.

Figure 5:
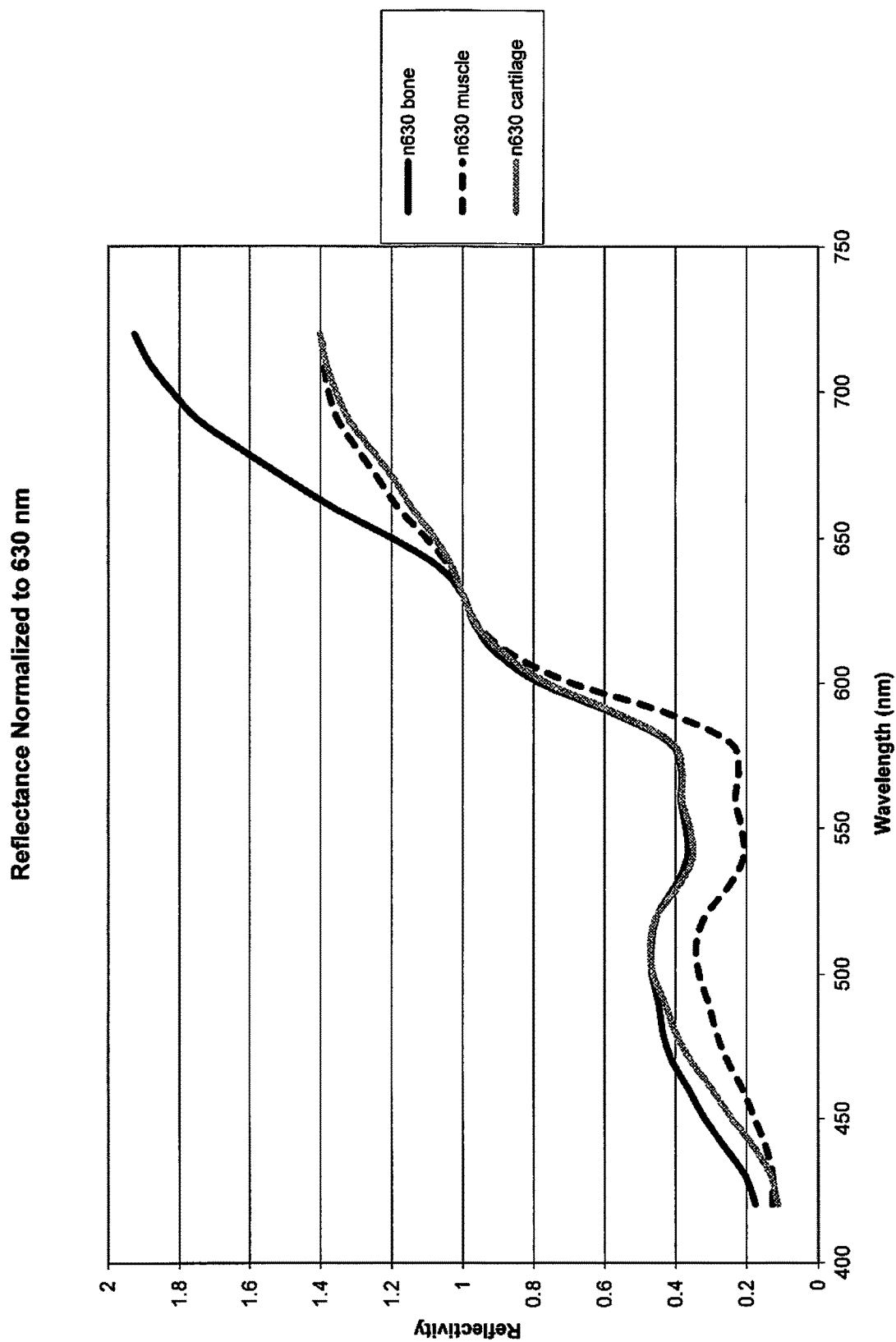
FIG. 5 shows a plot of reflectivity measured as against wavelength.

In FIG. 5 average reflectance spectra for regions of a chicken breast identified as bone, muscle, membrane, fat and cartilage are given in the range 420 to 720 nm. The spectra shown were obtained by averaging over pixels of the same tissue type and dividing the average at each wavelength by the average at 630 nm. The normalization compensates for variations caused by the irregular surface of the chicken breast. Each tissue type has a distinct average spectrum.

Figure 6:
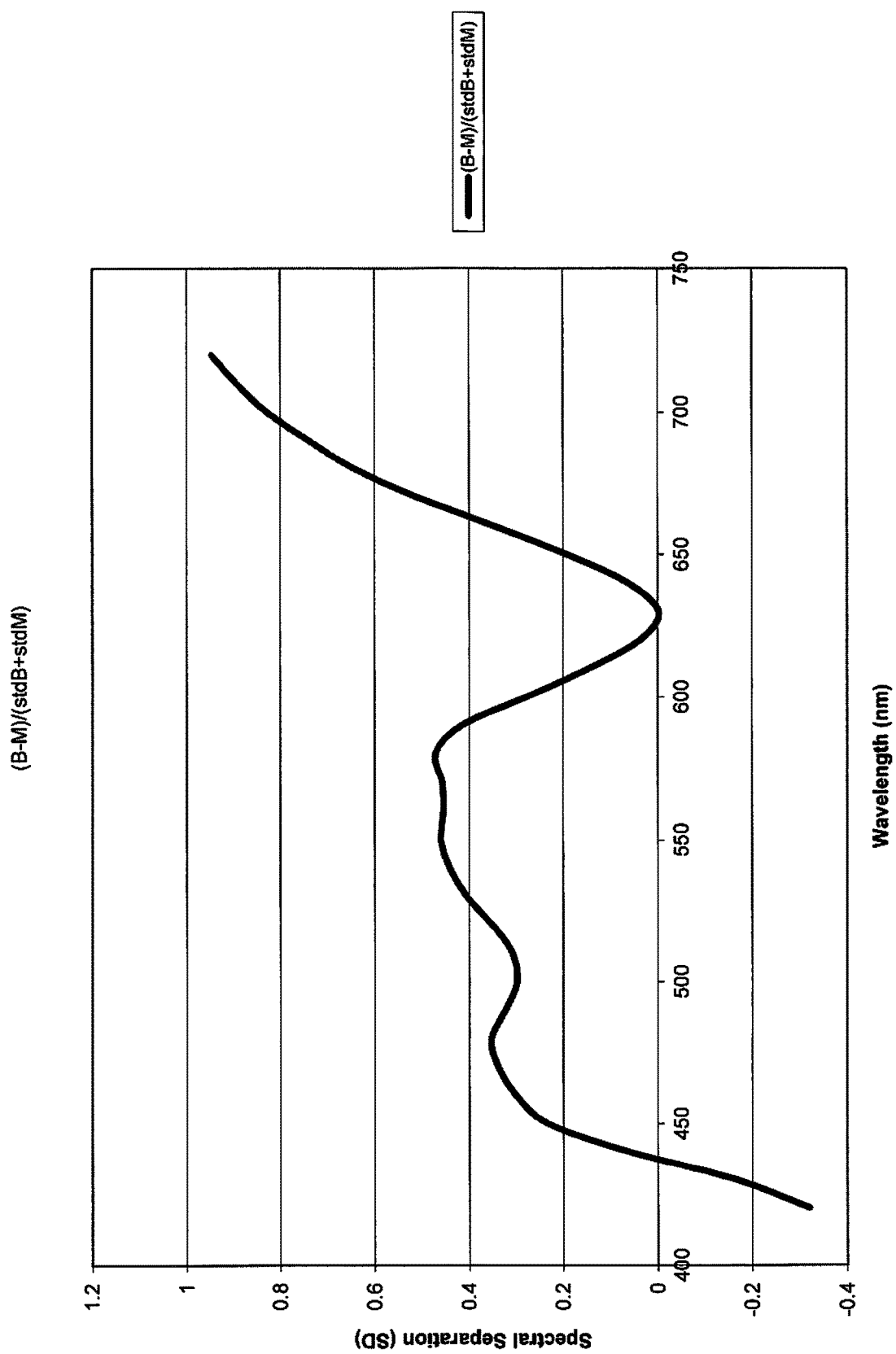
FIG. 6 shows a plot of spectral separation measured as against wavelength.

In FIG. 6 the spectral difference between bone and muscle is shown normalized by the sum of standard deviations in the range 420 to 720 nm. This plot shows the relative diagnostic value of each wavelength for distinguishing muscle and bone tissue. A larger ratio in absolute value indicates a higher probability of correctly distinguishing between muscle and bone at the level of an individual pixel. A small standard deviation (low variability) in the pixel population for a tissue type for a particular wavelength increases the utility of that wavelength for diagnostic purposes. Note the minimum near 630 nm where muscle and bone are statistically indistinguishable is a useful reference point for normalization.

The invention claimed is:

1. A method for detecting small objects wholly or partly embedded in a soft tissue sample, comprising the steps of:
emitting at least two wavelengths of light onto an area of said soft tissue sample;
receiving light reflected from said area of said soft tissue sample measuring the amplitude of said reflected light;
emitting at least one frequency of ultrasound onto said area of said soft tissue sample and receiving ultrasound signals returned from said soft tissue sample;
and in a data processor comparing the amplitudes of said reflected light for each said area of said soft tissue sample by multivariate analysis of amplitudes of a plurality of distinct wavelengths and determining from said multivariate analysis the presence of surface defects in said soft tissue sample using a statistical model;
wherein the statistical model calculates a cumulative probability that a defect exists within said area based on measurements of wavelength dependence, an edge probability obtained from a gradient of said amplitudes, and said acoustic signals loaded into a common data vector.

2. The method of claim 1 wherein a single wavelength of light is emitted and the reflected light is Raman scattered comprising the additional step of dispersing said Raman scattered light through a wavelength selector to separate the Raman scattered light into distinct wavelengths and the further additional step of measuring the amplitudes of said distinct wavelengths.

3. The method of claim 2 wherein said single wavelength is quasi monochromatic and selected from ultraviolet in the wavelength range of 200 to 220 nm and visible light and infrared light at 488, 515, 532, 594, 633, 635, 650, 660, 670, 780, 808, 830, 850, 980, and 1064 nm.

4. The method of claim 3 wherein said single wavelength ultraviolet is in the wavelength range of 200 to 220 nm.

5. The method of claim 2 wherein said single wavelength is selected from visible light and infrared light at 488, 515, 532, 594, 633, 635, 650, 660, 670, 780, 808, 830, 850, 980, and 1064 nm.

6. The method of claim 1 wherein said at least one wavelength of light is broad band white light and comprising the additional step of dispersing said reflected light through a wavelength selector to separate the reflected light into distinct wavelengths and the further additional step of measuring the amplitudes of said distinct wavelengths.

7. The method of claim 1 wherein said at least one wavelength of light is near infrared wavelength selected from the range of 900 to 2600 nm.

8. The method of claim 1 comprising the steps of emitting said at least two separate wavelengths at separate times for each wavelength, and the steps of measuring said amplitudes of reflected light at separate times for each wavelength.

9. The method of claim 8 wherein said at least two separate wavelengths comprise 620 to 640 and 720 to 760 nm.

10. The method of claim 8 wherein said at least two separate wavelengths comprise three wavelengths of 540 to 570, 620 to 640 and 720 to 760 nm.

11. The method of claim 8 wherein the steps of measuring the amplitudes of each separate wavelength are measured by the same focal plane array of pixels.

12. The method of claim 8 wherein the steps of measuring the amplitudes of each separate wavelength are measured by two separate focal plane arrays of pixels, each focal plane array measuring a different wavelength.

13. The method of claim 1 wherein said data processor receives a plurality of light amplitudes corresponding to a sample area of said soft tissue sample, said data processor generates n-dimensional data vectors from light amplitudes and compares said data vectors with a calibration set generated by multivariate analysis, to determine whether they correspond to bone, cartilage, fat, flesh or skin, or contaminant for each sample area of the sample, when undesired matter is identified, a logic signal is sent to actuate a pass-fail gate stopping the sample, otherwise no logic signal is sent.

14. The method of claim 13 wherein additionally said data processor identifies the amplitudes of neighboring areas to said sample area, abutting directly and diagonally, for each wavelength, calculates the gradient across said sample area and said abutting areas for all wavelengths and generates n-dimensional data vectors from said gradients and amplitudes, and compares said data vectors with a calibration set, generated by multivariate analysis, which additionally determines the presence of edges between sample areas, when undesired matter is identified, a logic signal is sent to actuate a pass-fail gate stopping the sample, otherwise no logic signal is sent.

15. The method of claim 1 wherein said data processor receives a plurality of acoustic amplitudes and times of flight of said amplitudes corresponding to a sample area of said soft tissue sample, said data processor compares said amplitudes to standard amplitudes to determine the presence of bone in said sample, when bone is present, a logic signal is sent to actuate a fail gate stopping the sample, otherwise no logic signal is sent.

16. The method of claim 1 wherein said data processor mean centers and normalizes said amplitudes to standard deviation for each wavelength.

17. The method of claim 1 wherein each type of LED of the same wavelength has a power converter controlled by a switching circuit, in combination with a logic processor, whereby each type of LED of the same wavelength is strobed separately.

* * * * *